United States Patent [19]

Haber et al.

[11] Patent Number: 5,443,827
[45] Date of Patent: Aug. 22, 1995

[54] FIBRIN-TARGETED INHIBITORS OF THROMBIN

[75] Inventors: Edgar Haber, Salisbury, N.H.; Christoph Bode, Heidelberg, Germany; Marschall S. Runge, Atlanta, Ga.

[73] Assignees: President and Fellows of Harvard College, Cambridge, Mass.; Emory University, Atlanta, Ga.

[21] Appl. No.: 58,699

[22] Filed: May 3, 1993

[51] Int. Cl.⁶ .................... A61K 39/395; C07K 16/00; C07K 16/18; C07K 7/50

[52] U.S. Cl. .................... 424/133.1; 424/145.1; 424/158.1; 424/178.1; 530/391.1; 530/388.25; 530/324; 530/387.3; 514/12

[58] Field of Search ............... 530/387.3, 388.25, 324, 530/391.1; 424/85.8, 133.1, 145.1, 158.1, 178.1; 514/12

[56] References Cited

U.S. PATENT DOCUMENTS

| | | | |
|---|---|---|---|
| 4,164,560 | 8/1979 | Folkman et al. | 424/22 |
| 4,767,742 | 8/1988 | Dodt et al. | 514/12 |
| 4,927,916 | 5/1990 | Matsueda et al. | 530/387 |
| 5,116,613 | 5/1992 | Haber et al. | 424/85.8 |
| 5,118,790 | 6/1992 | Winant et al. | 530/324 |
| 5,120,834 | 6/1992 | Gargan et al. | 530/388.25 |

FOREIGN PATENT DOCUMENTS 333356 9/1989 European Pat. Off. .

OTHER PUBLICATIONS

Hui, K. Y. et al., Science, 222:1129–1131, 1983.
Markwardt, F., Biomed Biochim. Acta, 44(Jul. 8):1007–1013, 1985.
Bode, C. et al., Clin. Cardiol, 13:375–381, 1990.
Waldmann, T. A., Science, 252:1657–1662, 1991.
Bode, C. et al., Circulation, 90:1956–1963, 1994.
Cadroy, Yves et al., J. Lab. Clin. Med., 114:349–57, 1989.
Hanson, Stephen R. et al., Arteriosclerosis, 5:595–603, Nov./Dec. 1985.
Schneider, P. A. et al., J. Vasc. Surg., 11:365–372, 1990.
Sheffield, W. P., et al., "Molecular Cloning and Expression of Rabbit Antithrombin III", Blood, vol. 79, No. 9, May 1, 1992; pp. 2330–2339.
Kim, B., et al., "Antithrombotic effect of β,β-monochloromethylene diadenosine 5',5'''-P1, P-4-tetraphosphate", Proc. Natl. Acad. Sci USA, vol. 89, Nov. 1992, pp. 11058.
Kettner, C., et al., "The Selective Inhibition of Thrombin by Peptides of Boroarginine", Journal of Biological Chemistry, vol. 265, No. 30, Oct. 25, 1990, pp. 18289–18297.
Kelly, A., et al., "Antithrombotic effects of synthetic peptides targeting various functional domains of thrombin", Medical Sciences, vol. 89, Jul. 1992, pp. 6040–6044.
Mor, A., et al., "Reaction of thrombin and proteinases of the fibrinolytic system with a mechanism-based inhibitor, 3,4-dihydro-3-benzyl-6-chloromethylcoumarin", Bio. et Biophysica Acta, 1038, 1990, pp. 119–124.
Schmaier, A. H., et al., "PPack-Thrombin is a Noncompetitive Inhibitor of α-Thrombin Binding to Human Platelets", Thrombosis Research, vol. 67, 1992, pp. 479–489.
Bagdy, D. et al., "Comparative Studies in vitro and Ex Vivo on the Anticoagulant Effects of a Reversible and an Irreversible Tripeptide Inhibitor of Thrombin", Thrombosis Research, vol. 67, 1992, pp. 221–231.
Sturzebecher, J., et al., "Interactions of Thrombin with Benzamidine-based Inhibitors", Biol. Chem. Hoppe-Seyler, vol. 373, 1992, pp. 491–496.

(List continued on next page.)

*Primary Examiner*—David L. Lacey
*Assistant Examiner*—Susan A. Loring
*Attorney, Agent, or Firm*—Fish & Richardson

[57] ABSTRACT

A chimeric molecule that contains a fibrin-binding portion of an antibody covalently linked to an inhibitor of thrombin, which molecule is administered to inhibit thrombus formation and growth.

14 Claims, 7 Drawing Sheets

OTHER PUBLICATIONS

Bode, W., et al., "Geometry of binding of the benzamidine- and arginine-based inhibitors Nx-(2-naphthyl-sulphonyl-glycyl) . . . to human α-thrombin", Eur. J. Biochem, vol. 193, 1990, pp. 175–182.

DiMaio, J., et al. "A new class of potent thrombin inhibitors that incorporates a scissile pseudopeptide bond", Fed. of Eur. Biochemical Societies, vol. 282, No. 1, Apr. 1991, pp. 47–52.

DiMaio, J., et al., "Synthesis of a Homologous Series of Ketomethylene Arginyl Pseudodipeptides and Appl. to Low Molecular Weight Hirudin-Like Thrombin Inhibitors", J. Med. Chem., vol. 33, 1992, pp. 3331–3341.

Runge, M. S., et al., "A recombinant chimeric plasminogen activator with high affinity for fibrin has incr. thrombolytic potency in vitor and in vivo", Proc. Natl. Acad. Sci USA, vol. 88, 1991, pp. 10337–10341.

Dodt, J., et al., "The complete amino acid sequence of hirudin, a thrombin specific inhibitor", Fed. of Eur. Biochemical Societies, vol. 165, No. 2, 1984, pp. 180–185.

Runge, M. S., et al., "Conjugation to an Antifibrin Monoclonal Antibody Enhances the Fibrinolytic Potency of Tissue Plasminogen Activator in Vitro", Biochemistry, vol. 27, 1988, pp. 1153–1157.

Bode, C., et al., "Characterization of an Antibody-Urokinase Conjugate", J. of Biological Chemistry, vol. 262, No. 22, 1987, pp. 10819–10823.

United States Serial No. 08/096,173, filed Jul. 26, 1993 (copy not available to us and not enclosed).

SEQUENCE LISTING (1) GENERAL INFORMATION:

(i i i) NUMBER OF SEQUENCES: 12

(2) INFORMATION FOR SEQ ID NO: 1:

(i) SEQUENCE CHARACTERISTICS:
        (A) LENGTH: 65
        (B) TYPE: amino acid
        (C) STRANDEDNESS:
        (D) TOPOLOGY: Linear (x i) SEQUENCE DESCRIPTION: SEQ ID NO: 1:

| Val | Val | Tyr | Thr | Asp | Cys | Thr | Glu | Ser | Gly | Gln | Asn | Leu | Cys | Leu |
|---|---|---|---|---|---|---|---|---|---|---|---|---|---|---|
| 1 | | | | 5 | | | | | 10 | | | | | 15 |
| Glu | Gly | Ser | Asn | Val | Cys | Gly | Gln | Gly | Asn | Lys | Cys | Ile | Leu | Gl |
| | | | 20 | | | | 25 | | | | | | 30 | |
| Asp | Gly | Glu | Lys | Asn | Gln | Cys | Val | Thr | Gly | Glu | Gly | Thr | Pro | Ly |
| | | 35 | | | | | 40 | | | | | 45 | | |
| Gln | Ser | His | Asn | Asp | Gly | Asp | Phe | Glu | Glu | Ile | Pro | Glu | Glu | Ty |
| | 50 | | | | | 55 | | | | | 60 | | | |
| Gln | | | | | | | | | | | | | | |
| 65 | | | | | | | | | | | | | | |

(2) INFORMATION FOR SEQ ID NO: 2:

(i) SEQUENCE CHARACTERISTICS:
        (A) LENGTH: 66
        (B) TYPE: amino acid
        (C) STRANDEDNESS:
        (D) TOPOLOGY: Linear (x i) SEQUENCE DESCRIPTION: SEQ ID NO: 2:

| Ile | Thr | Tyr | Thr | Asp | Cys | Thr | Glu | Ser | Gly | Gln | Asn | Leu | Cys | Leu |
|---|---|---|---|---|---|---|---|---|---|---|---|---|---|---|
| 1 | | | | 5 | | | | | 10 | | | | | 15 |
| Glu | Gly | Ser | Asn | Val | Cys | Gly | Lys | Gly | Asn | Lys | Cys | Ile | Leu | Gl |
| | | | 20 | | | | 25 | | | | | | 30 | |
| Gln | Gly | Lys | Asp | Asn | Gln | Cys | Val | Thr | Gly | Glu | Gly | Thr | Pro | Ly |
| | | 35 | | | | | 40 | | | | | 45 | | |
| Gln | Ser | His | Asn | Gln | Gly | Asp | Phe | Glu | Pro | Ile | Pro | Glu | Asp | Al |
| | 50 | | | | | 55 | | | | | 60 | | | |
| Asp | Glu | | | | | | | | | | | | | |
| 65 | | | | | | | | | | | | | | |

(2) INFORMATION FOR SEQ ID NO: 3:

(i) SEQUENCE CHARACTERISTICS:
        (A) LENGTH: 58
        (B) TYPE: amino acid
        (C) STRANDEDNESS:
        (D) TOPOLOGY: Linear (x i) SEQUENCE DESCRIPTION: SEQ ID NO: 3:

| Asp | Cys | Thr | Glu | Ser | Gly | Gln | Asn | Leu | Cys | Leu | Cys | Glu | Gly | Se |
|---|---|---|---|---|---|---|---|---|---|---|---|---|---|---|
| 1 | | | | 5 | | | | | 10 | | | | | 15 |
| Val | Cys | Gly | Gln | Gly | Asn | Lys | Cys | Ile | Leu | Gly | Ser | Asp | Gly | Glu |
| | | | 20 | | | | 25 | | | | | | 30 | |
| Asn | Gln | Cys | Val | Thr | Gly | Glu | Gly | Thr | Pro | Lys | Pro | Gln | Ser | Hi |
| | | 35 | | | | | 40 | | | | | 45 | | |

Asp Gly Asp Phe Glu Glu Ile Pro Glu Glu
         50                          55

(2) INFORMATION FOR SEQ ID NO: 4:

(i) SEQUENCE CHARACTERISTICS:
        (A) LENGTH: 12
        (B) TYPE: amino acid
        (C) STRANDEDNESS:
        (D) TOPOLOGY: Linear (xi) SEQUENCE DESCRIPTION: SEQ ID NO: 4:

Asn Gly Asp Phe Glu Glu Ile Pro Glu Glu Tyr Xaa
 1               5                   10

(2) INFORMATION FOR SEQ ID NO: 5:

(i) SEQUENCE CHARACTERISTICS:
        (A) LENGTH: 8
        (B) TYPE: amino acid
        (C) STRANDEDNESS:
        (D) TOPOLOGY: Linear (xi) SEQUENCE DESCRIPTION: SEQ ID NO: 5:

Phe Glu Glu Ile Pro Glu Glu Tyr
 1               5

(2) INFORMATION FOR SEQ ID NO: 6:

(i) SEQUENCE CHARACTERISTICS:
        (A) LENGTH: 16
        (B) TYPE: amino acid
        (C) STRANDEDNESS:
        (D) TOPOLOGY: Linear (xi) SEQUENCE DESCRIPTION: SEQ ID NO: 6:

Val Thr Gly Glu Gly Thr Pro Lys Pro Gln Ser His Asn Asp Gly Asp
 1               5                   10                      15

(2) INFORMATION FOR SEQ ID NO: 7:

(i) SEQUENCE CHARACTERISTICS:
        (A) LENGTH: 16
        (B) TYPE: amino acid
        (C) STRANDEDNESS:
        (D) TOPOLOGY: Linear (xi) SEQUENCE DESCRIPTION: SEQ ID NO: 7:

Val Thr Gly Glu Gly Thr Pro Asn Pro Glu Ser His Asn Asn Gly Asp
 1               5                   10                      15

(2) INFORMATION FOR SEQ ID NO: 8:

(i) SEQUENCE CHARACTERISTICS:
        (A) LENGTH: 12
        (B) TYPE: amino acid
        (C) STRANDEDNESS:
        (D) TOPOLOGY: Linear (xi) SEQUENCE DESCRIPTION: SEQ ID NO: 8:

Asn Gly Asp Phe Glu Glu Ile Pro Glu Glu Tyr Leu
 1               5                   10

(2) INFORMATION FOR SEQ ID NO: 9:

(i) SEQUENCE CHARACTERISTICS:
        (A) LENGTH: 20
        (B) TYPE: amino acid
        (C) STRANDEDNESS:
        (D) TOPOLOGY: Linear ( x i ) SEQUENCE DESCRIPTION: SEQ ID NO: 9:

Phe Pro Arg Pro Gly Gly Gly Gly Asn Gly Asp Phe Glu Glu Ile Pro
1           5                   10                  15
Glu Glu Tyr Leu
         20

( 2 ) INFORMATION FOR SEQ ID NO: 10:

( i ) SEQUENCE CHARACTERISTICS:
      ( A ) LENGTH: 7
      ( B ) TYPE: amino acid
      ( C ) STRANDEDNESS:
      ( D ) TOPOLOGY: Linear ( x i ) SEQUENCE DESCRIPTION: SEQ ID NO: 10:

Gly His Arg Pro Leu Asp Lys
1                 5

( 2 ) INFORMATION FOR SEQ ID NO: 11:

( i ) SEQUENCE CHARACTERISTICS:
      ( A ) LENGTH: 8
      ( B ) TYPE: amino acid
      ( C ) STRANDEDNESS:
      ( D ) TOPOLOGY: Linear ( x i ) SEQUENCE DESCRIPTION: SEQ ID NO: 11:

Gly His Arg Pro Leu Asp Lys Cys
1                 5

( 2 ) INFORMATION FOR SEQ ID NO: 12:

( i ) SEQUENCE CHARACTERISTICS:
      ( A ) LENGTH: 15
      ( B ) TYPE: nucleic acid
      ( C ) STRANDEDNESS: single
      ( D ) TOPOLOGY: linear ( x i ) SEQUENCE DESCRIPTION: SEQ ID NO: 12:

ATA GAA GGA CGA AGC           1 5
Ile Glu Gly Arg Ser
1             5

FIBRIN-TARGETED INHIBITORS OF THROMBIN

FIELD OF THE INVENTION

This invention relates to the inhibition of blood clot formation.

BACKGROUND OF THE INVENTION

Clot formation resulting in the blockage of a major coronary artery can lead to myocardial infarction, one of the most common causes of death in industrialized societies. Enzymatic recanalization of an occluded coronary artery with a drug such as streptokinase or tissue plasminogen activator (tpa) has been shown to reduce mortality significantly in patients suffering from acute myocardial infarction (Gruppo Italiano per lo Studio della Streptochinasi nell'Infarto Miocardico (GISSI) Lancet 2:871–874, 1987; Wilcox RG, Lancet 2:525–530, 1988; ISIS-2 Collaborative Study Group, Lancet 2:349–360, 1988). However, limitations of thrombolytic therapy include a very high rate of reocclusion (Gold et al., Circulation 73:347–352, 1986) and the relative resistance of arterial clots to lysis (Jang et al., Circulation 79:920–928, 1989). Acute thrombotic reocclusion is also a frequent and major setback after otherwise successful percutaneous transluminal coronary angioplasty (PTCA) (Detre et al., Circulation 80:421–428, 1989), and constitutes a formidable problem after the placement of intracoronary stents (Roubin et al., Circulation 85:916–927, 1992). Adjunctive therapy with currently available antiplatelet (ISIS-2 supra) and anticoagulant (Hsia et al., N Engl J Med 323:1433–1437, 1990) agents has shown some benefit in overcoming these difficulties and also in reducing restenosis (Hanke et al., Circulation 85:1548–1556, 1992).

Thrombin is an enzyme in blood that plays a central role in blood clot development by catalyzing the formation of fibrin from fibrinogen and, perhaps more importantly, as the most potent activator of platelets. The anti-coagulant, heparin, has been shown to be of only limited efficacy in antagonizing the action of thrombin in experimental studies. A number of direct inhibitors of thrombin have been shown to be effective in preventing platelet-dependent arterial thrombosis and rethrombosis after thrombolytic reperfusion in experimental animals (Haskel, Circulation 83:1048–1056, 1991; Jang et al., Circ. Res. 67:1552–1561, 1990; Heras et al., Circulation 82:1476–1484, 1990; Kelly et al., Blood 77:1006–1012, 1991; Sitko et al., Circulation 85:805–815, 1992). One of these thrombin antagonists is hirudin, an anti-coagulant derived from the leech, *Hirudo medicinalis* (Dodt et al., FEBS 165:180–184, 1984).

Plasminogen activators, such as streptokinase and urokinase, catalyze the conversion of plasminogen to its active fibrinolytic form, plasmin. These reagents activate circulating as well as fibrin-bound plasminogen and thus not only affect the lysis of fibrin in the thrombus, but also promote fibrinolysis elsewhere in the body. Tissue-type plasminogen activator has somewhat improved the specificity problem, but therapeutic administration of both fibrinolytic agents and thrombin inhibitors is still a problem because of their lack of selectivity and potential to cause generalized hemorrhaging.

SUMMARY OF THE INVENTION

The experiments described herein demonstrate that fibrin-specific antibody-targeted hirudin is more potent in inhibiting thrombus growth than hirudin alone because the local concentration of hirudin is increased by antibody binding to fibrin at the site of the thrombus. Clinical applications include localized inhibition of thrombosis as contrasted with systemic anti-coagulation. Anti-thrombin targeting of thrombin inhibitors can be especially useful in highly thrombogenic situations such as coronary stent implantation and can be used as an adjunctive therapy with highly selective thrombolytic agents.

Targeting of the thrombin antagonist has been accomplished by conjugating the antagonist to a fibrin-specific antibody, such as the monoclonal antibody termed 59D8. The epitope to which the 59D8 antibody binds becomes available only after thrombin cleaves fibrinopeptide B. It has been shown that 59D8 does not cross-react with uncleaved fibrinogen. Thus, only at sites where thrombin activity has become manifest will the anti-thrombin-conjugate locally accumulate and inhibit further thrombin action. This selectivity of inhibition, triggered by the very molecule that needs to be inhibited, permits a substantial reduction in the total amount of anti-thrombin activity that needs to be administered. Because inhibitor concentration would be concentrated at the thrombus, the plasma concentration of inhibitor required for anti-coagulation would be lower, thus resulting in a reduction in the potential for generalized hemorrhaging.

The invention features a chimeric protein containing an antagonist of thrombin activity linked to a fibrin-binding domain of an antibody. Preferably, the chimeric protein contains a thrombin antagonist linked to a fibrin-specific antibody, fibrin-specific Fab' fragment, or Fv fragment. The fibrin-binding domain of the antibody preferably does not bind to the fibrin precursor, fibrinogen. More preferably, the fibrin-binding domain is specific for the new amino terminus of the fibrin β chain that becomes exposed after thrombin has cleaved fibrinopeptide B. An example of such a fibrin-binding domain is that of monoclonal antibody 59D8. The portion of the chimera that inhibits thrombin activity is preferably hirudin or an active fragment or derivative of hirudin.

By the term "active fragment" is meant a peptide unconjugated to an antibody which has the ability to inhibit the action of thrombin with at least 50% of the thrombin inhibitory activity of the native hirudin as measured in the S-2238 chromogenic assay, described below.

The term "fragment" as applied to a polypeptide, denotes a peptide of the whole protein that can be proteolytically cleaved from the native protein, recombinantly expressed, or synthetically made, and is at least 6 contiguous residues. In this invention, a fragment is usually about 20 contiguous residues, preferably at least 40 contiguous residues, more preferably at least 50 contiguous residues, and most preferably at least 60 contiguous residues in length. Such peptides can be generated by methods known to those skilled in the art, including proteolytic cleavage of the protein, de novo synthesis of the fragment, or genetic engineering. Peptides can be made up of D- or L-amino acids or a mixture of both. Particularly preferred would be a peptide with a D-amino acid as the amino- or carboxyl-terminal amino acid, in order to inhibit proteolytic degradation of the chimeric protein.

Also within the invention are chemical derivatives of the above peptides. Chemical derivatives are defined as peptides to which one or more negatively charged side groups have been added. Derivatization methods, which are well known in the art, include but are not limited to sulfation, methyl sulfonation, phosphonation and carbonation of the tyrosine hydroxyl group; or sulfonation, phosphonation and carbonation of the tyrosine benzoyl meta carbon. Preferably, either or both termini of the chimeric protein would be protected from proteolytic degradation by the presence of a standard protective group such as an aidehyde. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

The components of the chimeric protein are joined using a covalent bond, such as a disulfide bond. In another embodiment, the chimeric protein is produced recombinantly, with the two components of the chimera joined by a peptide bond.

The therapeutic method of the invention specifies the administration of the chimeric protein in a pharmaceutically suitable vehicle. The invention further specifies introduction of the chimera into the circulatory system of an animal. In another embodiment, the chimeric proteins are introduced into or contacted with blood that has been removed from the individual, followed by the return of treated blood to the animal.

The invention also includes a mixture of the chimeric protein of the invention with another chimeric protein that contains a fibrin-binding domain of an antibody linked to a fibrinolytic agent, e.g., as disclosed in U.S. Pat. No. 5,116,613, herein incorporated by reference. The fibrin-specific antibody portion of the second chimera may be identical to or different from that of the first chimera. The thrombin antagonist is preferably hirudin, whereas the fibrinolytic agent is preferably streptokinase, staphylokinase, urokinase, or tissue-type plasminogen activator. The mixture of proteins is introduced into the circulatory system of an animal to dissolve and prevent further formation of aberrant blood clots. In another embodiment, the mixture is introduced into blood that has been removed from the animal for treatment, and subsequently returned to the animal.

The invention also features a nucleic acid encoding the chimeric protein and a cell that contains the nucleic acid and expresses the protein, as well as the therapeutic administration of the nucleic acid to an individual to prevent coagulation of blood. Such cells may be useful, for example, in a therapeutic method of introducing into an animal (e.g., a human patient), cells that have been transfected with and express the chimeric protein.

Also included in the invention is a therapeutic method of preventing and dissolving blood clots that specifies the administration of the nucleic acid encoding the chimeric protein and the nucleic acid encoding a second chimeric protein that contains a fibrin-binding domain linked to a fibrinolytic agent. More preferably, the therapeutic method specifies the administration of two populations of cells, one of which contains and expresses nucleic acid encoding the chimeric protein of the invention, and a second population of cells that produces a chimeric protein that contains a fibrin-binding domain linked to a fibrinolytic agent.

The invention includes a nucleic acid encoding a recombinant chimeric protein containing an antagonist of thrombin activity linked to a fibrin-specific antibody and a cell expressing the recombinant chimeric protein.

Also within the invention is a method of administering into the blood of a patient a nucleic acid encoding such a chimeric protein, either alone or together with a nucleic acid encoding a chimeric protein that contains a fibrin-binding domain linked to a fibrinolytic agent, as well as a method of separate or simultaneous administration of cells expressing each of the recombinant proteins.

BRIEF DESCRIPTION OF THE DRAWINGS

FIG. 2A: hirudin-59D8IgG conjugate (●—●) versus hirudin (○—○). FIG. 2B: hirudin-59D8-Fab' conjugate (●—●) versus hirudin (○—○). Each point represents mean of three independent experiments.

FIG. 4A shows a time course of fibrin deposition by hirudin or hirudin-59D8-IgG conjugate, on the surface of a clot suspended in a fibrinogen solution: hirudin at 80 ATU/ml (□—□), 8 ATU/ml (○—○), 2.4 ATU/ml (◇—◇) and hirudin-59D8-IgG conjugate at 7.4 ATU/ml (●—●), 1.2 ATU/ml (◆—◆). FIG. 4B is a graph depicting inhibition of fibrin formation on the surface of a clot suspended in a fibrinogen solution as a function of thrombin inhibition by hirudin (○—○) or hirudin-59D8-IgG conjugate (●—●) at 120 minutes. Each point in FIG. 4B represents the mean of three replicates.

FIG. 5A is a graph showing a time course of fibrin deposition on the surface of a clot suspended in a fibrinogen solution by hirudin or hirudin-59DS-Fab' conjugate: hirudin at 100 ATU/ml (□—□), 30 ATU/ml (○—○), 10 ATU/ml (◇—◇) and hirudin-59D8-Fab' conjugate at 9.25 ATU/ml (◆—◆), 3 ATU/ml (●—●), 0.1 ATU/ml (◆—◆). FIG. 5B is a graph depicting fibrin deposition on the surface of a clot suspended in a fibrinogen solution as a function of thrombin inhibition by hirudin (○—○) or hirudin-59D8-Fab' conjugate (●—●) at 180 minutes. Each point in FIG. 5B represents the mean of three replicates.

FIG. 6A is a graph showing the time course of fibrin deposition on the surface of a clot suspended in human plasma by hirudin or hirudin-59D8-Fab' conjugate: hirudin at 100 ATU/ml (○—○), 10 ATU/ml ( — ), hirudin-59D8-Fab' conjugate at 10 ATU/ml (●—●), 1 ATU/ml (◆—◆) and NaCl control (x—x). FIG. 6B is a graph showing inhibition of fibrin formation on the surface of a clot suspended in human plasma as a function of thrombin inhibition by hirudin (○—○) or hirudin-59D8-Fab' conjugate (●—●) at 120 minutes. Each point in FIG. 6B represents the mean of three replicates.

DETAILED DESCRIPTION

Figure 1A:
FIG. 1A and FIG. 1B are photographs of hirudin-59D8-Fab' conjugate and its parent molecules separated using sodium dodecylsulfate-polyacrylamide gel electrophoresis (SDS-PAGE) (12.5% gel) and stained with Coomassie-blue; electrophoresis was performed under non-reducing (FIG. 1A) and reducing (FIG. 1B) conditions. Lane 1, molecular weight standards; lane 2, 59D8-Fab'; lane 3, final preparation of hirudin-59D8-Fab' conjugate; lane 4, hirudin. The molecular weight standards were phosphorylase b (94) kDa), bovine serum albumin (67 kDa), ovalbumin (43 kDa), carbonic anhydrase (30 kDa), soybean trypsin inhibitor (20.1 kDa), and lactalbumin (14.4 kDa).

In accordance with the present invention, specific targeting of anti-thrombotic agents to the surface of a clot was studied. The thrombin antagonist, hirudin, which is capable of inhibiting fibrin-bound thrombin, was conjugated to the anti-fibrin antibody 59D8 and the fibrin-specific Fab'-fragment of 59D8. 59D8 binds selectively to the new amino-terminus of the fibrin β-chain that becomes exposed after thrombin cleaves fibrinopeptide B (Hui et al., Science 222:1129–1131, 1983), an early event in clot formation. Targeting of hirudin in this manner results in a dramatic reduction of fibrin deposition at the very site of thrombin action and clot growth.

Reagents

The chromogenic substrate, S-2238 (H-D phenylalanyl-L-pipecolyl-L-arginine-p-nitroaniline dihydrochloride), was obtained from Chromogenix, Mödlndal, Sweden. N-Succinimidyl-3-(2-pyridyldithio) propionate (SPDP) was purchased from Pierce Chemical (Rockford, Ill.), and $^{125}$I-labelled fibrinogen was obtained from Amersham (Arlington Heights, Ill.). Fresh frozen plasma was purchased from the University of Heidelberg blood bank and the German Red Cross. All other chemicals were purchased from Sigma Chemical, St. Louis, MO.

Hirudin

Recombinant Hirudin having the sequence of the native protein (Dodt et al., FEBS 1104 165:180–184, 1984, herein incorporated by reference) (SEQ ID NO:i) [r-Hirudin LU 52369, specific activity: 17,000 anti-thrombin units (ATU)/mg] was obtained from Knoll AG, Ludwigshafen, Germany. Fragments and derivatives of hirudin with anti-thrombin and anti-coagulant activity are known in the art, such as Hirudin PA (SEQ ID NO:2) (Dodt, J. et al., U.S. Pat. No. 4,767,742); a polypeptide defined by the sequence X-AA$_3$-[AA$_4$-AA$_{62}$]-AA$_{63}$-Z, where AA$_3$ is a conservative amino acid residue other than tyrosine that is not susceptible to electrophilic chemical modification, AA$_4$-AA$_{62}$ is amino acids 4–62 of the native hirudin sequence (Dodt et al. FEBS 1104 165:180–184, 1984) (SEQ ID NO:3), AA$_{63}$ is a tyrosine residue or a tyrosine residue modification so as to contain an electron-withdrawing substituent in the 3-, or 3-, 5-positions of the phenyl ring, X is hydrogen or an N-terminal extension sequence corresponding to some or all of the native hirudin sequence, and Z is a hydroxyl group or a C-terminal extension corresponding to some or all of the native hirudin sequence (Winant, R. C. et al., U.S. Pat. No. 5,118,790); peptides characterized by the sequence Asn-Gly-Asp-Phe-Glu-Glu-Ile-Pro-Glu-Glu-Tyr-X (SEQ ID NO:4) and D-retro forms thereof, where X can be COOH, Leu or Leu-Gln; or the sequence Y-Phe-Glu-Glu-Ile-Pro-Glu-Glu-Tyr-Z (SEQ ID NO:5) and D-retro forms thereof, where Y can be NH$_2$, an amino protecting group, at least the C-terminal portion of the amino acid sequence: Val-Thr-Gly-Glu-Gly-Thr-Pro-Lys-Pro-Gln-Ser-His-Asn-Asp-Gly-Asp (SEQ ID NO:6), or at least the C-terminal portion of the amino acid sequence: Val-Thr-Gly-Glu-Gly-Thr-Pro-Asn-Pro-Glu-Ser-His-Asn-Asn-Gly-Asp (SEQ ID NO:7), and Z can be COOH, Leu, or Leu-Gln; and the tyrosine residue is characterized by the presence of a negatively charged side group (Maranganore, J. M., European Patent Application 333356). Each of the above references is herein incorporated by reference.

Thrombin Inhibitors

Other thrombin inhibitors are known in the art, such as antithrombin III (Sheffield et al., Blood 79:2330–2339, 1992); β, β' monochlormethylene diadenosine 5'5'''-P$^1$p$^4$-tetraphosphate (Kim et al., Proc. Natl. Acad. Sci. USA 89:11056–11058,1992); boroarginine peptides, such as Ac-(D)Phe-Pro-boroArg-OH, Boc-(D)Phe-pro-boroArg-C$_{10}$H$_{16}$, H-(D)Phe-Pro-boroArg-OH, and H-(D)Phe-Pro-boroArg-C$_{10}$H$_{16}$ (Kettner et al., J. Biol. Chem. 265:18289–18297, 1990); synthetic peptides, such as D-Phe-Pro-Arg (CSAP), [Asn-Gly-AsP-Phe-Glu-Glu-Ile-Pro-Glu-Glu-Tyr-(OSO3)-Leu (SEQ ID NO:8), the sulfated C-terminal dodecapeptide of hirudin](ESAP), and [D-Phe-Pro-Arg-Pro-(Gly)4-Asn-Gly-Asp-phe-Glu-Glu-Ile-Pro-Glu-Glu-Tyr-Leu] (SEQ ID NO:9) (BAP) (Kelly et al., Proc. Natl. Acad. Sci. USA 89:6040–6044, 1992); 3,4,-dihydro-3-benzyl-6-chloromethylcoumarin (Mor et al., Biochim Biophys Acta 1038:119–124, 1990); D-phenylalanyl-prolylarginine chloromethyl ketone-treated e-thrombin (PPACK-IIa) (Schmaier et al., Thromb. Res. 67:479–489, 1992); tripeptide inhibitors, such as D-Phe-Pro-Arg-H (ALD) and D-Phe-Pro-Arg-CH$_2$-Cl (CMK) (Bagdy et al., Thromb. Res. 67:221–231, 1992); benzamidine-based inhibitors such as Nε-(β-naphthylsulfonylglycyl)-4-amidinophenylalanine piperidide (NAPAP) (Sturzebecher et al., Biol. Chem. Hoppe-Seyler 373:491–496, 1992); and arginine-based inhibitors such as (2R,4R)-4-methyl-1-[N$^α$-(3-methyl-1,2,3,4-tetrahydro-8-quinolinesulphonyl) -L-arginyl]-2-piperidine carboxylic acid (MQPA) (Bode et al., Eur. J. Biochem. 193:175–182, 1990); thrombin inhibitors incorporating a scissile peptide bond, such as N$^α$-acetyl[D-Phe$^{45}$, ArgΨ(COCH$_2$)$^{47}$, Gly$^{48}$]desulfo hirudin$^{45-65}$ (P79) (DiMaio et al., FEBS Lett. 282:47–52, 1991); and ketomethylene pseudopeptides, such as [Ac-(D)-Phe$^{45}$,Pro$^{46}$, ArgΨ(COCH$_2$)CO$^{47,48}$,Gly$^{49}$-]Hirudin$^{45-65}$ (Hirutonin-1), [Ac-(D)-Phe$^{45}$,Pro$^{46}$, ArgΨ[COCH$_2$]CH$_2$CO$^{47}$]Hirudin$^{45-65}$ (Hirutonin-2), [Ac-(D)-Phe$^{45}$,Pro$^{46}$,ArgΨ[COCH$_2$]CH$_2$CH$_2$CO$^{47,48}$-]Hirudin45–65 (Hirutonin-3), and [Ac-(D)-Phe$^{45}$,Pro$^{46}$,ArgΨ[COCH$_2$]CH$_2$CH$_2$CO$^{47,48}$]Hirudin$^{45-65}$ (Hirutonin-4) (DiMaio et al., J. Med. Chem. 35:3331–3341, 1992). The above references pertaining to thrombin inhibitors are herein incorporated by reference.

Fibrin-specific antibodies

Monoclonal anti-fibrin antibody 59D8 (ATCC Accession No. HB 8546) was prepared and purified as previously described (Matsueda et al., U.S. Pat. No. 4,916,070, herein incorporated by reference). The method for the production of other fibrin-specific monoclonal antibodies lacking fibrinogen cross-reactivity is described in detail in Matsueda et al., U.S. Pat. No. 4,927,916, herein incorporated by reference.

Example 1: Chemically conjugated Hirudin-59D8 IgG and Hirudin-59D8 Fab'

Preparation of 59DS-IgG conjugate

The disulfide-linked hirudin-IgG conjugates were prepared by reacting an N-Succinimidyl 3-(2-pyridyldithio) propionate (SPDP) derivative of hirudin with 2-iminothiolane-substituted anti-fibrin monoclonal antibody 59D8. 8 mg hirudin were dissolved in 2 ml 50 mM sodium carbonate buffer, pH 8.5. Subsequently, 2 ml of n-propanol were added. SPDP was added in 3-fold molar excess (20 mM in absolute ethanol) dropwise to the hirudin solution. This mixture was stirred gently at room temperature for 3 min and then applied to a Sephadex G-25 column (1.6×90 cm) that had been equilibrated with PBS (0.1M $NaH_2PO_4$, 0.1M NaCl, pH: 7.4). Peak protein fractions were pooled and analyzed for 2-pyridyldisulfide content (Carlsson et al., Biochem J. 173:723–737, 1978) and typically showed 0.6–1.5 residues per hirudin molecule. The SPDP substitution level was kept intentionally low to limit loss of hirudin activity and to avoid formation of higher molecular-weight aggregates. Specific activity of SPDP-modified hirudin was on average 53% that of unmodified hirudin.

Other thrombin antagonists can be modified with reagents, such as SPDP or succinimidyl 4-(N-maleimidomethyl)cyclohexane-1-carboxylate (SMCC), to add a single terminal thiol-reactive group. Other antagonists modified in this manner can then be conjugated to 2-iminothiolane-substituted anti-fibrin antibody or fibrin-specific Fab' or Fv.

Anti-fibrin monoclonal antibody 59D8 was raised against β-peptide, Gly-His-Arg-Pro-Leu-Asp-Lys (SEQ ID NO:10). Monoclonal antibody 59D8 (4 mg/ml in 0.14M NaCl, 3.7 mM $Na_2PO_4$, mM KCl, pH 7.4) was mixed in equal amounts (v/v) with a 1,000-fold molar excess of 2-iminothiolane (in 25 mM sodium borate, pH 9.3). The reaction was allowed to continue for 25 min at room temperature with gentle stirring. Excess iminothiolane was removed by gel filtration on Sephadex G-25 that had been pre-equilibrated with PBS, pH 6.6. A 10-fold molar excess of the SPDP-modified hirudin was then mixed with the iminothiolated antibody, with gentle stirring at room temperature for 5 hours. The reaction was stopped by the addition of 10-fold molar excess (compared to the hirudin concentration) of iodoacetamide in 0.1M $Na_2HPO_4$, pH 8.0.

Preparation of 59DS-Fab' conjugate

The (Fab')$_2$ of antibody 59D8 was obtained by pepsin cleavage according to standard methods. It was then affinity purified on a β-peptide Sepharose affinity column, made by coupling a synthetic β-peptide, Gly-His-Arg-Pro-Leu-Asp-Lys-(Cys) (SEQ ID NO:11), to lysine-Sepharose via the cysteine residue, using maleimidobenzoylsuccinimide ester. The eluate of this column (0.2M glycine, pH 2.8) was dialyzed against PBS and found to contain only (Fab')$_2$ and traces of Fab' or Fab, as assessed by SDS-PAGE. Reduction of the 59D8 (Fab')$_2$ was carried out at room temperature for 18 hours in 1 mM 2-mercaptoethylamine, 1 mM EDTA, 10 mM sodium arsenite, followed by the addition of solid Ellman's reagent (SIGMA Chemical Company, St. Louis, MO) to a concentration of 5 mM. After 3 h at room temperature, excess reagent was removed by gel filtration on a Sephadex G-25 column (30×2 cm) and equilibrated with 0.1M sodium phosphate pH 6.8. In this protected form, 59D8 Fab' remains structurally and functionally intact at 4° C. under sterile conditions for at least 1 year. The thiol form of 59D8 Fab' was easily regenerated by treatment with 10 mM 2-mercaptoethylamine for 30 minutes at room temperature, followed by gel filtration.

Chimetic proteins can also be made by linking fibrin-specific Fv fragments to thrombin antagonists. Fv fragments can be made according to methods known in the art (Anthony et al., Mol. Immunol. 29:1237–1247, 1992; Huston et al., Proc. Natl. Acad. Sci USA 85:5879–5883, 1988) and then modified to introduce a sulfhydryl group by 2-iminothiolane substitution as described above.

The thiol form of 59D8 Fab' (at 1 mg/ml) was mixed with SPDP-modified hirudin (1 mg/ml) and allowed to react for 16 hours at room temperature. To minimize the amount of uncoupled 59D8 Fab' in the final preparation, hirudin was present in the mixture in a 10-fold molar excess. The reaction was stopped by addition of an excess of iodoacetamide, as described above.

The thiol form of 59D8 Fv or other fibrin-specific Fab' or Fv fragments can be conjugated to hirudin as described above.

Purification of 59D8 conjugates

The hirudin-59DS-IgG conjugate and the hirudin-59DSFab' conjugate were both partially purified from the reaction mixture by affinity chromatography on a β-peptide-Sepharose column. The affinity column retains the conjugated as well as unconjugated 59DS-IgG or 59DS-Fab', but not uncoupled hirudin. The eluate (0.2M glycine, pH 2.8) from this column was dialyzed into PBS and stored under sterile conditions at 4° C. Alternatively, uncoupled hirudin may be removed from the reaction mixture by gel-filtration on Sephadex G-100.

Electrophoresis and densitometric scanning

SDS-PAGE was performed according to the method of Laemmli (Laemmli et al., Nature 227:680–685, 1970), and proteins were visualized by staining with Coomassie brilliant blue G-250 (Neuhoff et al., Electrophoresis 9:255–262, 1988). For relative protein quantitation, the gels were scanned at 633 nm with an LKB ultrascan XL laser-densitometer. Quantitation was made on unreduced gels which provide separate bands for hirudin-conjugated 59DS-IgG and unconjugated 59DS-IgG or hirudin-conjugated 59D9-Fab' and unconjugated Fab'.

Protein determination

Protein concentrations were assayed according to Lowry (with bovine serum albumin used as a standard) (Lowry, J. Biol Chem 193:265–275, 1951), or by measuring optical density at 280 nm.

Quantitation of hirudin activity (S-2238 assay)

The S-2238 assay measures thrombin activity and its inhibition by anti-thrombins. To 100 μl of sample hirudin or hirudin-59D8 conjugate in assay buffer (20 mM sodium dihydrogen carbonate, 0.15M NaCl, 0.1% BSA, pH 7.4), 20 μl of thrombin solution (2.5 U/ml water) were added and incubated at room temperature for 10 min. Then 50 μl (0.833 mg/ml) of chromogenic substrate S-2238 (H-D phenylalanyl-L-pipecolyl-L-arginine-p-nitroaniline dihydrochloride) were added. After exactly 5 min of incubation, the reaction was stopped by addition of 50 μl 20% acetic acid, and the test result was read at 405 nm. Quantitation was obtained by comparing inhibition of thrombin activity in the test sample with that achieved by different known concentrations of unconjugated hirudin. A linear relationship was achieved with certainty for anti-thrombin concentrations between 0 and 0.6 U/ml hirudin-activity, and samples with higher activity were diluted appropriately.

β-Peptide assay 96-well microtiter plates were coated overnight at 4° C. with β-peptide. 100 μl coating buffer (20 mM Tris, 50 mMNaCl, 1 mM $CaCl_2$, 1 mM $MgC_2$, pH 7.4) containing 0.005 mg β-peptide were applied to each well. After coating, the microtiter plate was first washed 5 times with coating buffer supplemented with 0.05% Tween 20 and then three times with water. Free binding sites were blocked overnight at 4° C. by the addition of 250 μl bovine serum albumin (2% w/v in coating buffer) per well. The washing step was repeated and defined amounts (by the S-2238 assay) of either hirudin or hirudin-59D8 conjugate (hirudin-59D8 IgG or, alternatively, hirudin-59D8 Fab' in 0.1M NaCl, 0.1M $NaPO_4$, pH 7.4) were applied in 100 μl of buffer per well and incubated for 2 h at room temperature. Samples were run in triplicate.

After washing 7 times with modified coating buffer (20 mM Tris, 0.5 M $NaCl_2$, 1 mM $CaCl_2$, 1 mM $MgCl_2$, 0.2% Tween 20, pH 7.4) and three times with water, 100 μl of assay buffer (20 mM $NaHPO_4$, 0.15M NaCl, 0.1% BSA, pH 7.4) were applied per well and 20 μl (1.25 U/ml) of thrombin solution were allowed to incubate for 1 h at room temperature. Then 50 μl of chromogenic substrate (S-2238 at 0.83 mg/ml) were applied and after 20 minutes, the reaction was stopped by addition of 50 μl of 20% acetic acid, and the resulting absorption read at 405 nm. Hirudin activity was detected as inhibition of thrombin activity and was expressed as % inhibition of total thrombin activity applied.

Fibrin-Sepharose assay

This assay is as described by Bode et al., J. Biol. Chem. 262:10819–10823, 1987, herein incorporated by reference, with the following modifications. For the purposes of assaying targeted anti-thrombin activity, trace labeling of fibrin-monomer is not necessary. 200 μl fibrin-Sepharose were incubated for 2.5 h at room temperature with defined amounts (by the S-2238 assay) of hirudin or hirudin-59D8-conjugate (hirudin-59D8-IgG or, alternatively, hirudin-59D8-Fab') in 100 μl of buffer. After washing the fibrin-Sepharose three times with 3 ml 0.15M NaCl, 200 μl S-2238 assay buffer and 40 μl (0.05 U) thrombin solution (1.25 U/ml) were added and incubated for 1 h at room temperature. Subsequently 100 μl of chromogenic substrate S-2238 were added, and the reaction was stopped after 25 min by addition of 100 μl 20% acetic acid. After centrifugation (5 min, 1,000×g), absorption of the supernatant was read at 405 nm. Hirudin activity was again detected as inhibition of thrombin activity and was expressed as % of total thrombin activity applied.

Inhibition of thrombus growth in a fibrinogen solution

The method of Runge (Runge et al., Biochemistry 27:1153–1157, 1988, herein incorporated by reference) was followed, with the following modifications. Fresh-frozen plasma obtained from 5 donors was pooled, aliquoted and refrozen. Before each experiment, plasma was ultracentrifuged at 30,000 rpm for 60 min in a Beckmann SW 40 rotor in order to obtain platelet-free plasma (platelet count less than 1,000 platelets/μl). Immediately before each experiment, the anti-thrombin activities of hirudin and hirudin conjugate were calibrated using the S-2238 assay (i.e., the inhibition of thrombin peptidase activity by hirudin and its conjugates was determined, and appropriate dilutions were made so that the inhibition of thrombin peptidase activity was identical for each sample). Platelet-free plasma clots were made by adding to plasma, in the following sequence: $^{125}$I-labelled human fibrinogen (20,000 cpm/ml plasma), 0.5M $CaCl_2$ (final concentration 0.05M) and thrombin (0.5 NIH units/ml plasma). Immediately after the addition of thrombin, the solution was drawn into silastic tubing (i.d. 4 mm) and allowed to clot for 2 h at 37° C. The tubing was then cut into 1.8 cm sections yielding clots of approximately 0.2 ml. The clots were removed from the tubing, and each was placed in a plastic vial and washed three times with 2 ml 0.15M NaCl. The radioactivity level of each was then determined and only clots within 5% of the mean value were used for experiments.

After counting, clots were resuspended in 100 μl TBS (0.1M Tris, 0.1M NaCl, pH 7.4). Experiments were initiated by the addition of 100 μl hirudin or conjugate solution containing defined amounts of anti-thrombin activity. Then, 200 μl of fibrinogen solution (8 mg/ml) trace labelled with $^{125}$I-fibrinogen (25,0000 cpm/ml) were added to the clot. The final fibrinogen concentration in the test assay was thus in the physiological range (4 mg/ml). At predetermined intervals, clots were removed from the test tube, washed three times with 2 ml 0.15M NaCl and assayed for radioactivity. Clots incubated without thrombin inhibitor (NaCl-controls) often could not be quantitatively removed from the incubation vial because of complete clotting of the assay mixture.

Inhibition of thrombus growth in human plasma

These assays were executed as described above. Clots were incubated with 200 μl of platelet-free plasma (instead of 200 μl of fibrinogen solution) and trace labelled with $^{125}$I-fibrinogen (250,000 cpm/ml).

Statistical Analysis

Figure 2A:
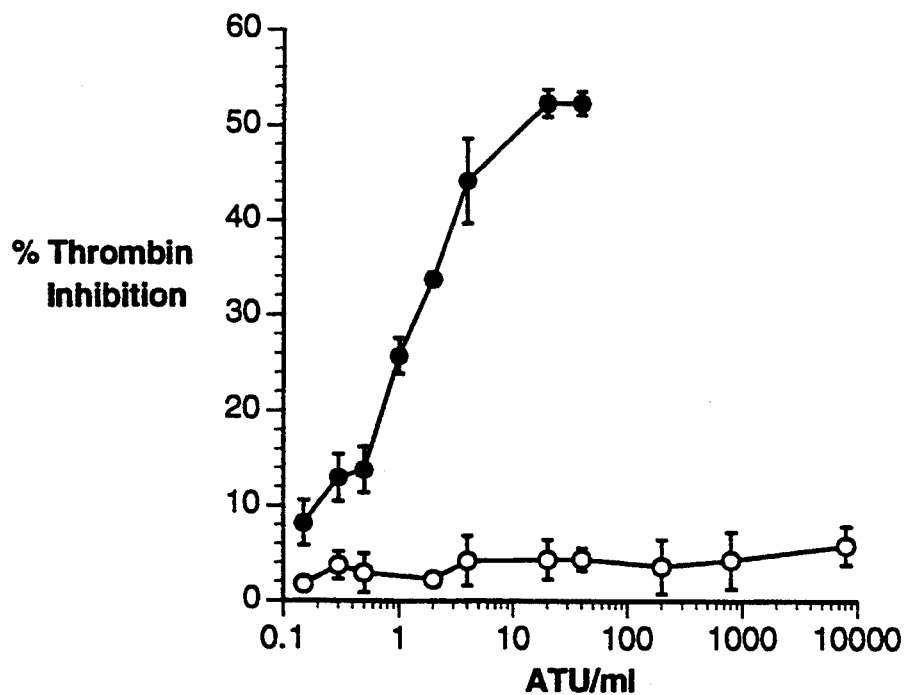
FIG. 2A and FIG. 2B are graphs depicting thrombin inhibition as a function of binding to an immobilized target molecule, $\beta$-peptide. Hirudin-dependent inhibition of thrombin-mediated cleavage of chromogenic substrate, S-2238, was recorded at 405 nm and expressed as a percentage of inhibition of total thrombin added.
Figure 2B:
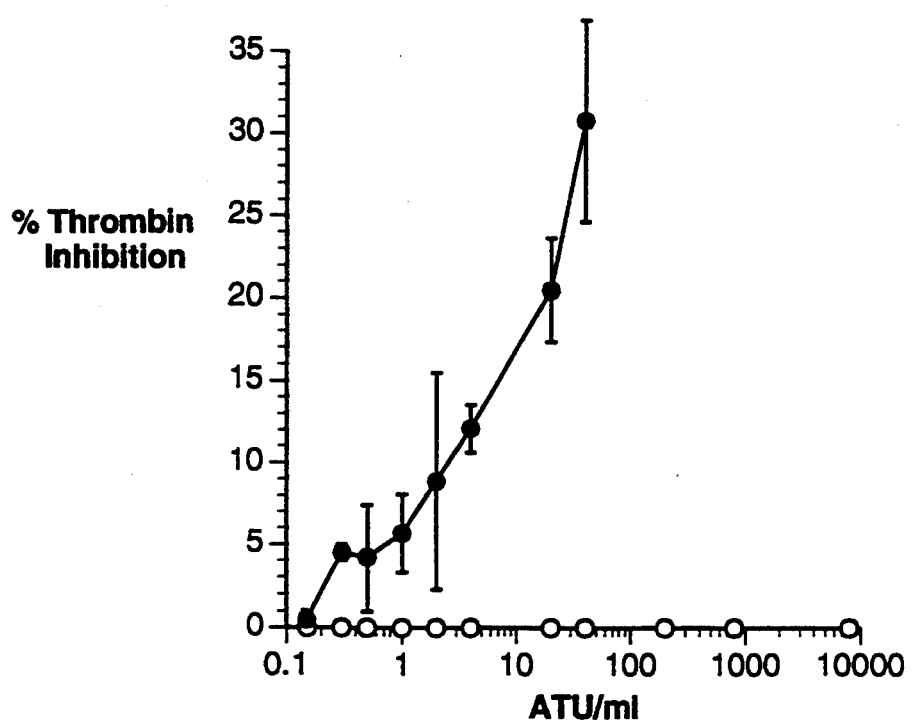
Figure 3A:
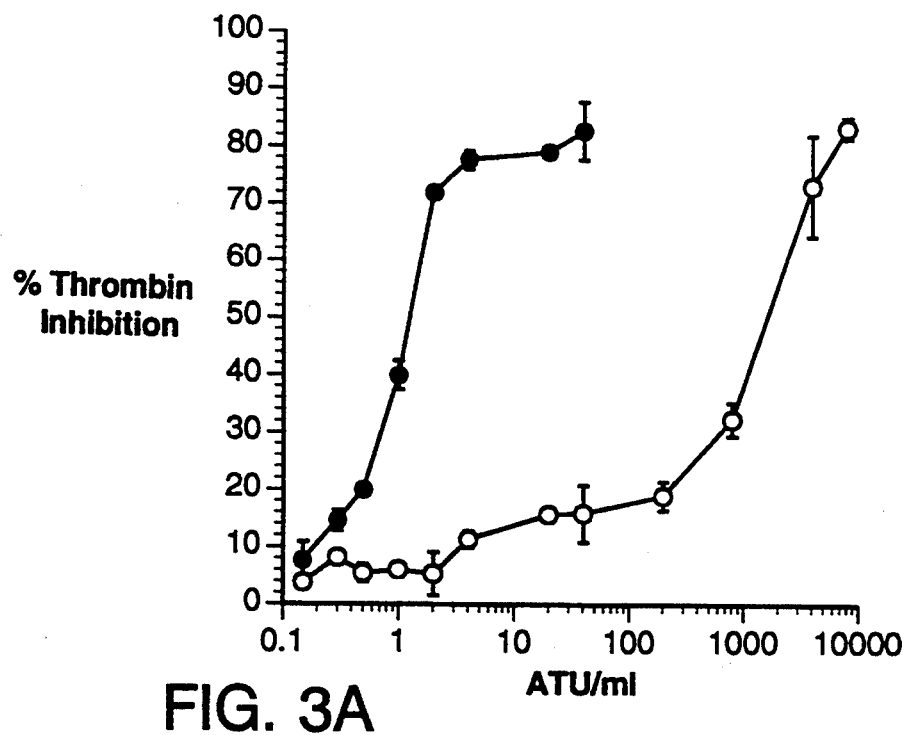
FIG. 3A and FIG. 3B are graphs depicting thrombin inhibition (% of total) plotted against applied concentration of thrombin inhibitor in the fibrin-Sepharose assay. Each data point represents the mean of three independent experiments. Thrombin inhibitors in FIG. 3A are hirudin-59D8-IgG conjugate (●—●) and hirudin (○—○), and in FIG. 3B, hirudin-59D8-Fab' conjugate (●—●) and hirudin (○—○).
Figure 3B:
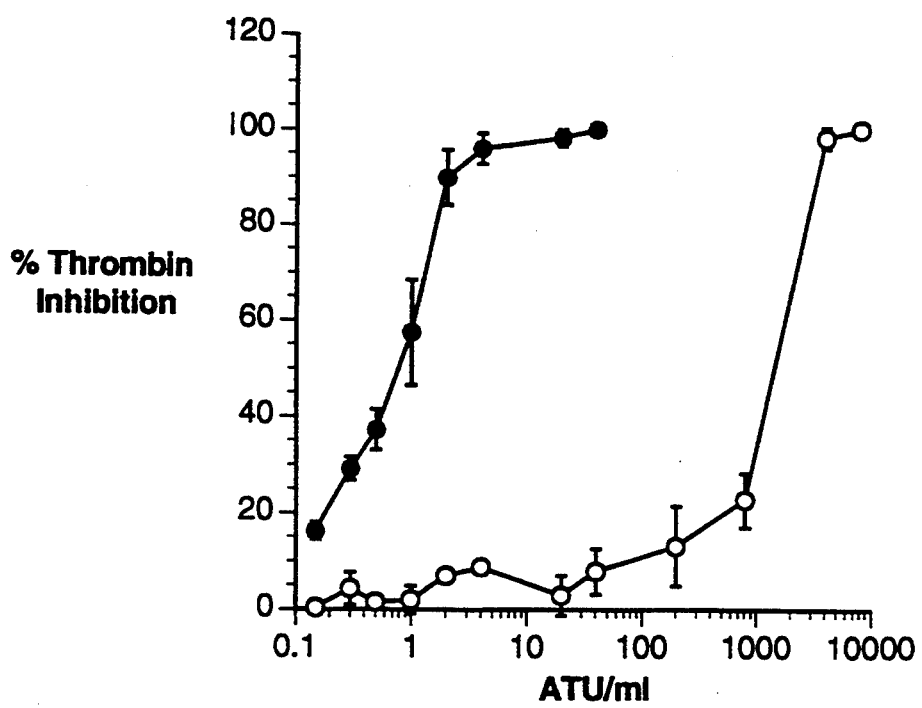

The dose-response curves in FIGS. 2 and 3 were compared (hirudin-59D8 conjugate versus unconjugated hirudin control within each assay) by fitting each curve with the antilogit function:

$$\% \text{ Thrombin inhibition } (ATU) = B1 \cdot \frac{e^{B2(ln(ATU)-ln(ATU0))}}{1 + e^{B2(ln(ATU)-ln(ATU0))}}$$

where B1 is the ultimate thrombin inhibition of infinite concentration of inhibitor, B2 is the rate constant for the increase in inhibition with increasing concentration (ATU) of inhibitor, and $ATU_0$ is the concentration of inhibitor (in ATU/ml) at which ½ the ultimate (B1) inhibition is achieved. For each curve the three parameters B1, B2 and $ATU_0$ and the variances for each parameter were estimated by using the FIT FUNCTION procedure of the RS/1 Data Analysis Software (BBN Software Products, Cambridge, MA). Corresponding parameters (B1, B2 and $ATU_0$) for each curve were compared by the t test.

The time-course curves describing fibrin deposition in FIGS. 4, 5, and 6 were compared by batching fibrin values for each curve across all three time points and then, after confirming by one way analysis of variance (ANOVA ONEWAY procedure, RS/1 software) that significant differences existed among some of the curves, performing t tests on the mean fibrin deposition values (in μg) for each curve. This procedure served as a means of protecting against detecting excessive differences due to multiple comparisons.

The dose-response curves in FIGS. 4, 5, and 6 were compared by first performing linear regression analysis of fibrin deposition versus dose of inhibitor for each inhibitor separately and then comparing the slopes and intercepts of the regression lines by the t test. The FIT FUNCTION procedure (RS/1 software) was used to estimate the variances of the linear regression parameters.

Figure 7:
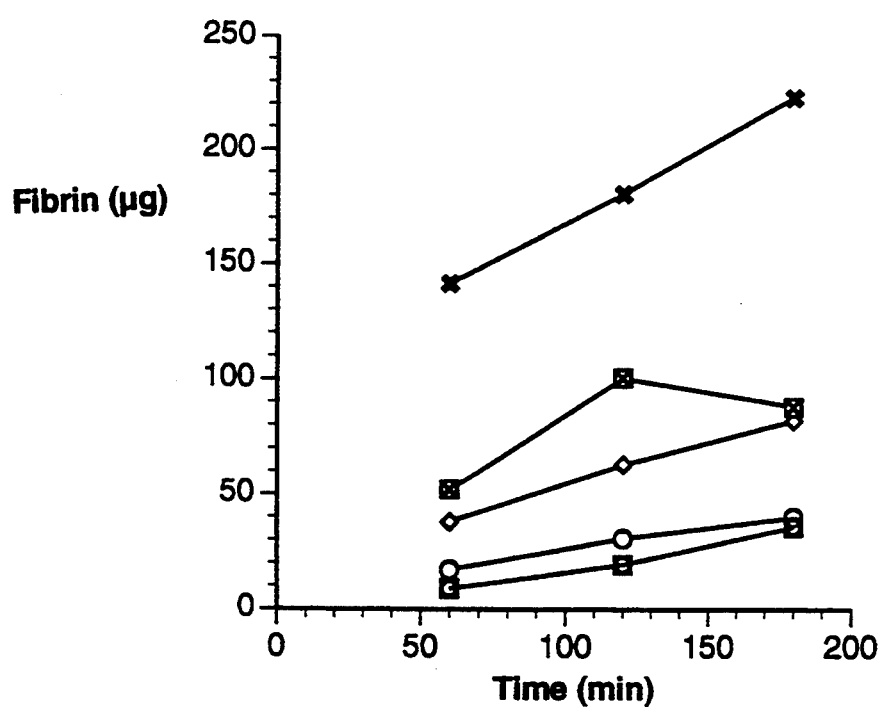
FIG. 7 is a graph showing a time course of fibrin deposition on the surface of a clot suspended in human plasma for hirudin and a 1:3 molar mixture of uncoupled hirudin and 59D8 Fab': hirudin at 44 ATU/ml (o—o) and 10 ATU/ml (◊—◊); mixture at 43 ATU/ml (□—□) and 9 ATU/ml ■— ; and NaCl control (x—x).

The time-course curves in FIG. 7 were sufficiently linear to permit analysis of covariance, with time as a covariate. This analysis tested the hypothesis that the time course of fibrin deposition was identical among the various inhibitors (with and without the NaCl control). The analysis of covariance was followed by pairwise planned comparisons (linear contrasts) of the various inhibitor curves (P4V procedure, BMPD Statistical Software, University of California Press, Berkeley and Los Angeles, 1990).

All error estimates cited are standard deviations of the estimates. Potency differences are expressed by the ratios of the estimated $ATU_0$ parameters.

Characterization of hirudin-59DS-IgG and hirudin-59D8-Fab, conjugates

The nature of the disulfide-linked conjugates obtained by coupling SPDP-modified hirudin either to iminothiolane-modified antibody or to Fab' was defined in part by the coupling conditions and by the purification procedure.

The biological activity of hirudin is sensitive to SPDP-modification, because intact, unmodified lysine-47 is essential for its anti-thrombin effects. Therefore, basic reaction conditions, which lead to preferential modification of the amino-terminus of the protein, were chosen. Furthermore, SPDP was used at a low concentration in order to introduce not more than one reactive group into the hirudin molecule. Even when prepared under the above conditions, however, SPDP-hirudin was on average only 53% as active as unmodified hirudin in the S-2238 chromogenic assay for thrombin inhibition.

The conjugate was partially affinity purified on a β-peptide-Sepharose column. The eluate contained the desired hirudin-59DS-IgG or hirudin-59D8-Fab' conjugate as well as unconjugated 59DS-IgG or 59DS-Fab'. In order to minimize the amount of uncoupled IgG or Fab', a 10-fold molar excess of modified hirudin was used in the reaction mixture.

Figure 1B:
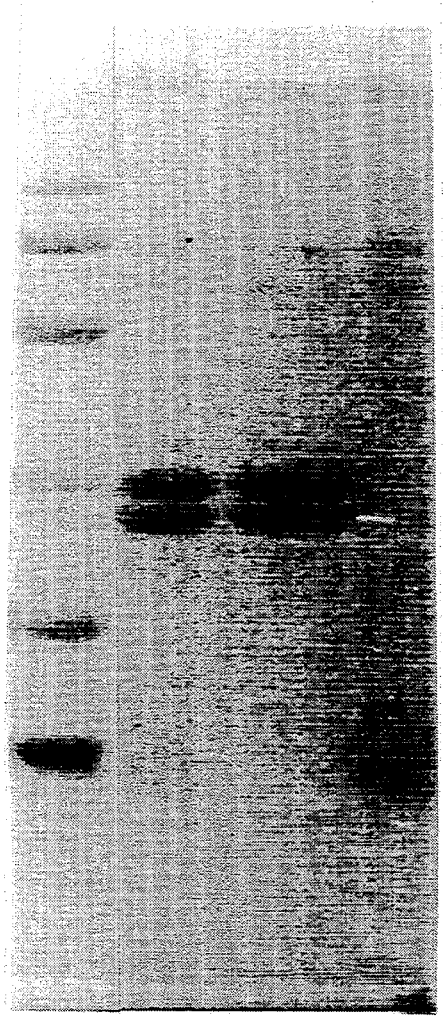

Both the parent molecules and the conjugates were analyzed by SDS-PAGE under reducing and non-reducing conditions (FIG. 1A and FIG. 1B). When electrophoresed under non-reducing conditions (FIG. 1A), the hirudin-59D8-Fab' conjugate (lane 3) was visualized at 57 kDa. A 1:1 molar ratio of hirudin and 59DS-Fab' was to be expected because each molecule contained only one reactive sulfhydryl group. However, the chemistry and the procedure used to purify hirudin-59D8-Fab' conjugate did not completely remove unconjugated 59D8-Fab', which migrates at 50 kDa (compare lane 2: 59DS-Fab'). When electrophoresed under reducing conditions (FIG. 1B), the disulfide bond linking hirudin to 59D8-Fab' was broken and the two chains of 59D8-Fab' could be visualized (lane 2 for 59D8-Fab' and lane 3 for hirudin -59D8-Fab'). Hirudin stained poorly under these conditions.

Densitometric quantitation of the bands revealed an approximately 1:1 molar ratio of hirudin-59D8-Fab' conjugate and uncoupled 59D8-Fab' in the final preparation used for the assays described below.

Thrombin inhibition in the absence of fibrin (the target molecule)

The thrombin inhibitory activity of hirudin was compared with that of hirudin-59D8-IgG conjugate or hirudin-59DS-Fab' conjugate in the absence of the target molecule, fibrin, by measuring inhibition of thrombin peptidase activity. Thrombin-dependent cleavage of the chromogenic substrate, S-2238, was recorded at 405 nm. The inhibitory activities of hirudin and hirudin-59D8-IgG conjugate or hirudin-59D8-Fab' conjugate were made comparable at all concentrations tested and at all time points recorded after an appropriate calibration procedure. In subsequent experiments, appropriate dilutions of hirudin-59D8 IgG, and hirudin-59D8 Fab' were used so that inhibition of thrombin peptidase activity was identical for each experimental point.

Thrombin inhibition as a function of hirudin binding to β-peptide

Thrombin inhibitory activities of hirudin and hirudin-59D8-IgG conjugate or hirudin-59D8-Fab' conjugate were compared as a function of binding to immobilized β-peptide, the antigen against which the antibody had been raised. This assay was designed to maximize the functional differences among the tested molecules. After thrombin inhibitory activity of each species had first been assessed in the absence of β-peptide, samples with identical thrombin inhibitory activity were then assayed with β-peptide as a target molecule. FIG. 2A shows that the hirudin-59D8 IgG conjugate was twelve-fold more potent than hirudin in an assay that depends on binding to the β-peptide ($B_1 = 55 \pm 2\%$ versus $4.3 \pm 0.5\%$, $p < 0.0001$). Hirudin-59D8 Fab' was as potent as the IgG conjugate (FIG. 2B). At $32.5 \pm 3.5\%$, ultimate inhibition by the Fab' conjugate was significantly greater than that by unconjugated hirudin (0%; $p < 0.0001$). This difference indicates that a single antigen binding site of the antibody is sufficient for effective targeting. Both conjugates performed significantly better than hirudin. The reason for this large difference is the specific binding of the conjugates to the immobilized target molecule through the 59D8-IgG or 59D8-Fab' antigen-combining site, whereas unconjugated hirudin, which is incapable of specific binding to the target molecule, is washed out.

Thrombin inhibition as a function of hirudin binding to immobilized fibrin

Hirudin, hirudin-59D8-IgG conjugate and hirudin-59D8-Fab' conjugate were compared in the fibrin-Sepharose assay as follows: after thrombin inhibitory activity of each species had first been assessed in the absence of fibrin, samples with identical thrombin inhibitory activity were then assayed with fibrin as a target molecule. FIG. 3 shows that at the highest level of thrombin inhibition, hirudin-59D8 IgG was 1100-fold more potent ($p < 0.0001$) and hirudin-59D8 Fab' was 1900-fold more potent ($p < 0.0001$) than unconjugated hirudin. 800 units of hirudin were required to achieve 32.3% thrombin inhibition, whereas only 1 unit of hirudin-59D8-IgG conjugate was required to obtain 39.9% inhibition and 0.5 units of hirudin-59D8-Fab, conjugate required to achieve 37.2% inhibition of thrombin.

Inhibition of thrombus growth in fibrinogen solution

Figure 4A:
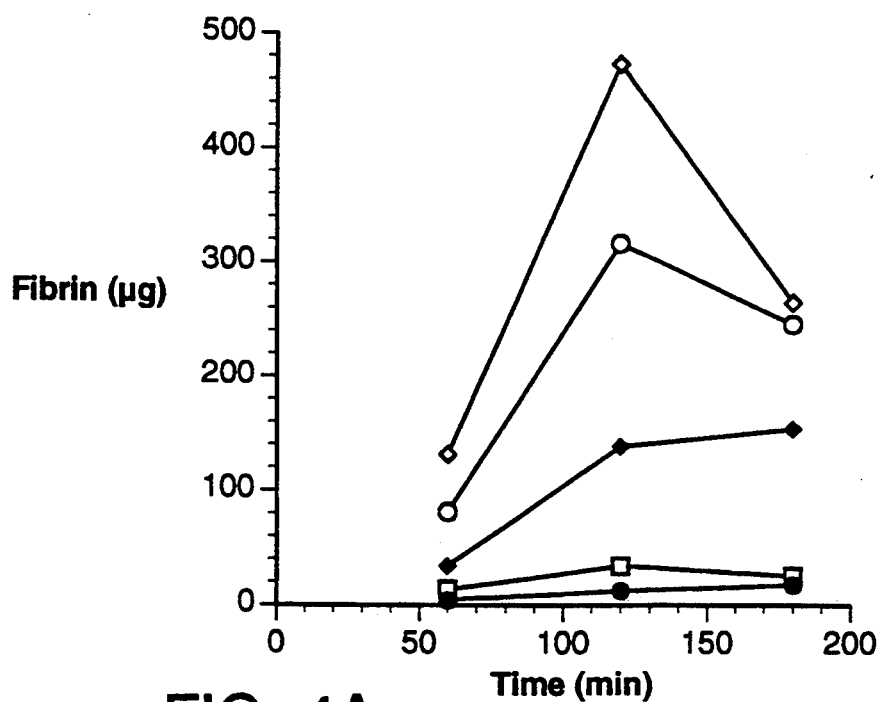
FIG. 4A and FIG. 4B are graphs illustrating fibrin deposition on the surface of a plasma clot.

The inhibition of fibrin formation on the surface of a plasma clot suspended in Tris-buffer containing fibrinogen at physiological concentration is shown in FIG. 4. Complete inhibition of fibrin formation for 3 h was achieved using 7.4 ATU/ml of hirudin-59D8-IgG conjugate, compared to 80 ATU/ml hirudin (FIG. 4A). Conjugate at 7.4 ATU/ml allowed significantly less fibrin deposition than hirudin at 8 ATU/ml (233 µg less, $p = 0.0002$) and hirudin at 2.4 ATU/ml (252 µg less, $p = 0.0001$). Conjugate at 1.2 ATU/ml allowed significantly more fibrin deposition than hirudin at 80 ATU/ml (113 µg more, $p = 0.01$).

Figure 4B:
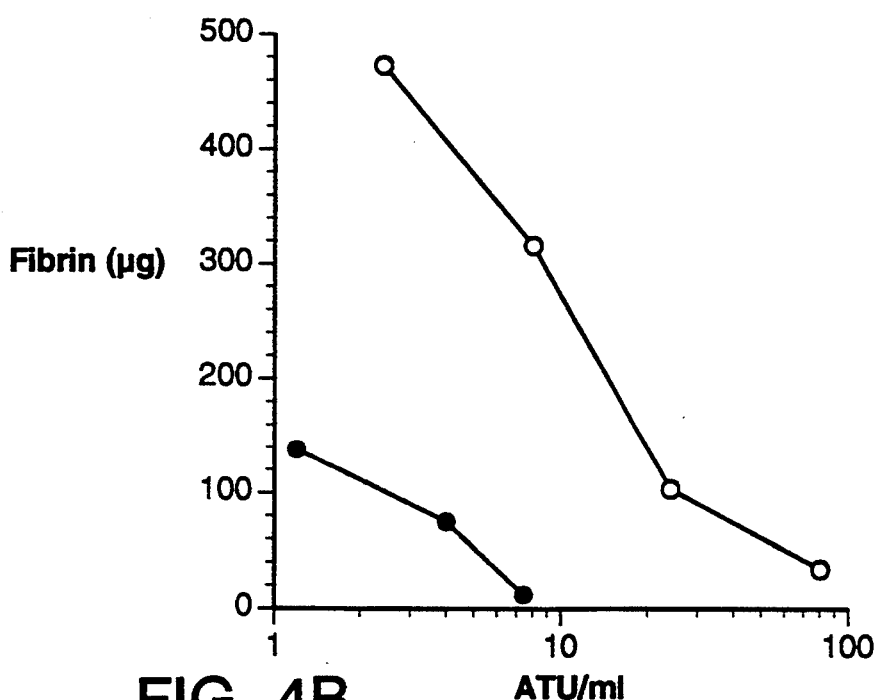

When fibrin deposition was plotted against inhibition of thrombin peptidase activity, hirudin-59D8 IgG conjugate was about 10 times more effective than hirudin (FIG. 4B). The intercept fibrin deposition for hirudin-59D8 IgG was significantly lower than that for unconjugated hirudin ($p = 0.003$). The slopes were the same.

Figure 5A:
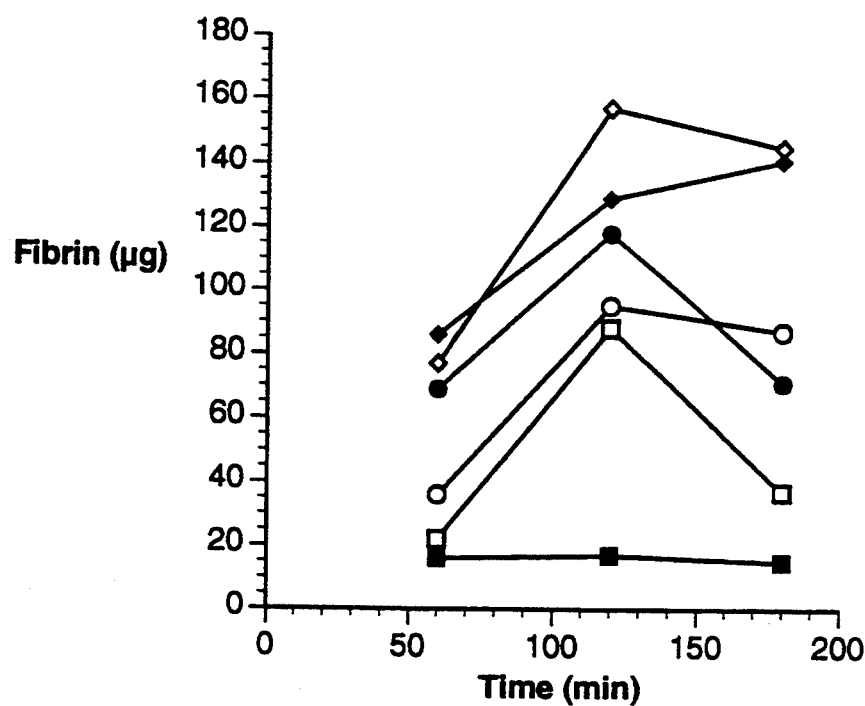
FIG. 5A and FIG. 5B are graphs showing fibrin deposition in fibrinogen solution.
Figure 5B:
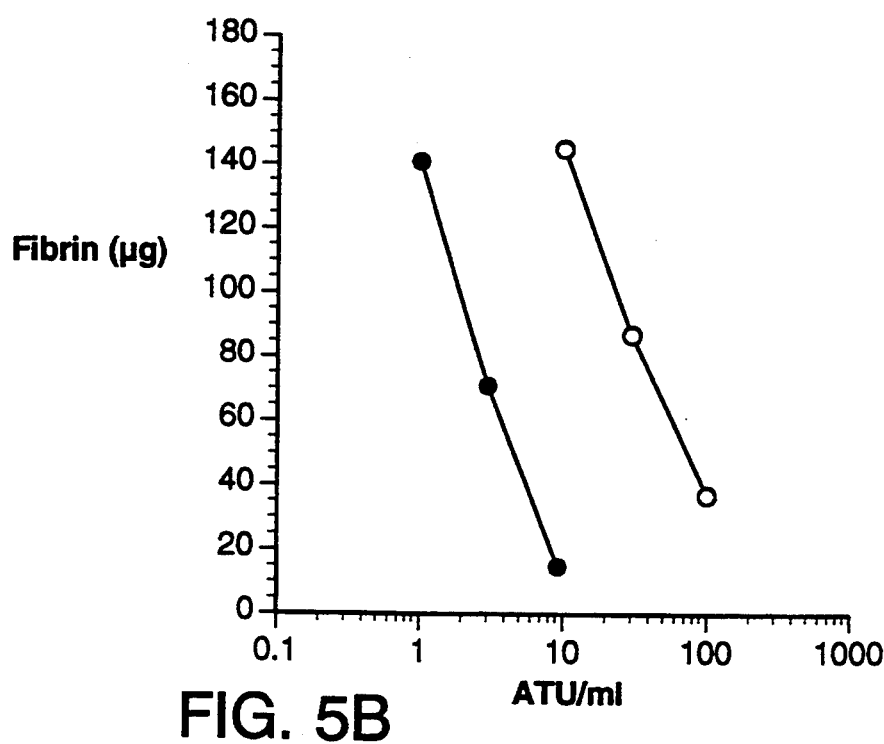

Results for hirudin-59D8 Fab' were similar (FIG. 5). Fibrin deposition for hirudin-59D8 Fab' at 9.25 ATU/ml was 21 µg lower than that for hirudin at 100 ATU/ml ($p = 0.001$), 71 µg lower than that for hirudin at 30 ATU/ml ($p = 0.0001$), and 129 µg lower than that for hirudin at 10 ATU/ml ($p = 0.0001$) (FIG. 5A). Also, fibrin deposition for hirudin-59D8 Fab' at 3 ATU/ml was significantly lower, by 74 µg, than that for hirudin at 10 ATU/ml ($p = 0.01$). All other fibrin deposition curves were indistinguishable. For the dose-response curves (FIG. 5B), the intercept fibrin deposition for hirudin-59D8 Fab' significantly lower than that for unconjugated hirudin ($p = 0.003$); the slopes were equal.

Figure 6A:
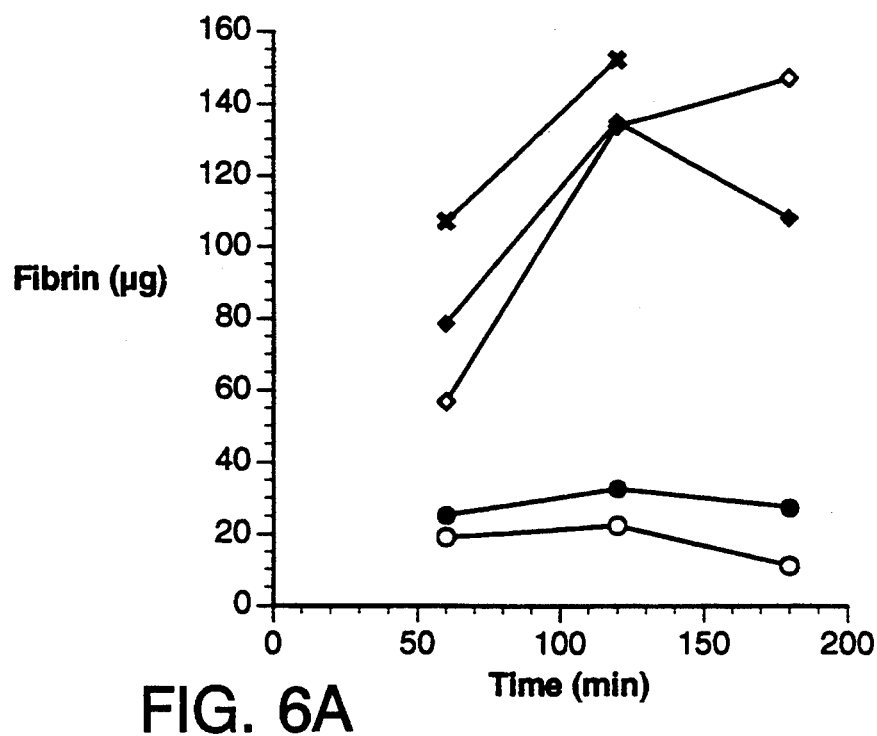
FIG. 6A and FIG. 6B are graphs showing fibrin deposition in human plasma.

Inhibition of thrombus growth in human plasma:

The enhanced potency of hirudin-59DS-Fab' conjugate was also demonstrated in human plasma. FIG. 6A shows that fibrin deposition was 84 µg lower for conjugate at 10 ATU/ml than for hirudin at 10 ATU/ml ($p = 0.0001$), and 101 µg lower than for NaCl control ($p = 0.0001$), whereas deposition was indistinguishable from that for hirudin at 100 ATU/ml. Fibrin deposition for the conjugate at 1 ATU/ml was 90 µg higher than that for hirudin at 100 ATU/ml ($p = 0.0001$) and was indistinguishable from that for hirudin at 10 ATU/ml or that for the NaCl control. Fibrin deposition for hirudin at 100 ATU/ml was 112 µg lower than that for the NaCl control ($p = 0.0001$). With a 17 µg lower mean fibrin deposition over time, hirudin at 10 ATU/ml was no different than the NaCl control.

Figure 6B:
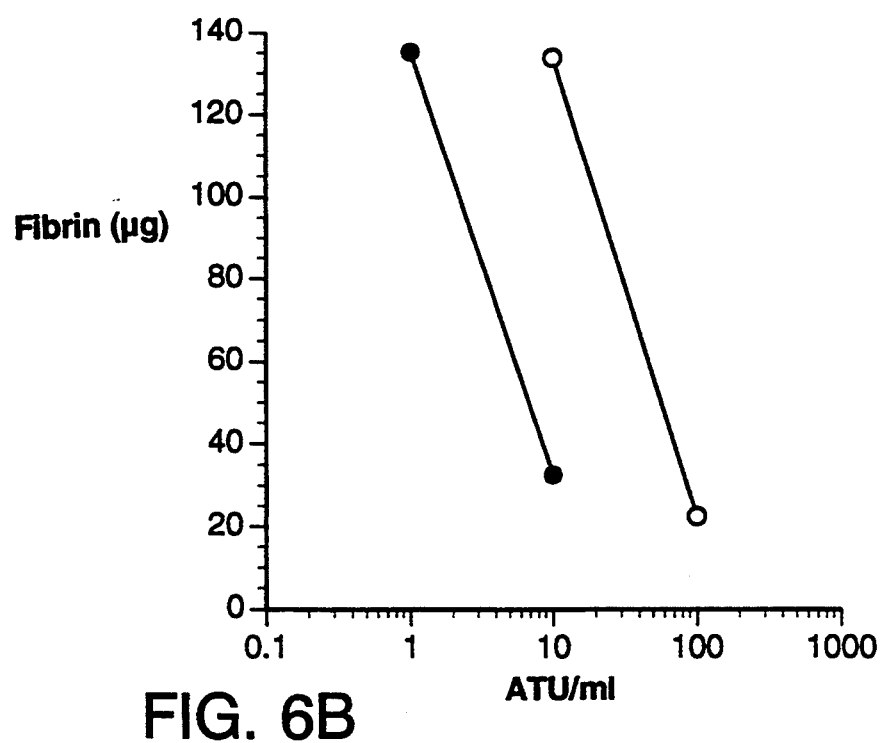

For the dose-response cures in FIG. 6B, the intercept fibrin deposition for hirudin-59D8 Fab' was significantly lower than that for hirudin. These results in plasma were similar to those in fibrinogen solution (compare FIGS. 5B and 6B); in both systems, the fibrin-targeted hirudin conjugate is 10 times more potent than hirudin.

Comparison of Hirudin with a Mixture of Hirudin and Antibody

To exclude any influence of uncoupled antibody or Fab' on the activity of hirudin, an equimolar mixture of the two components was compared with hirudin alone. FIG. 7 shows that the mixture of components was not significantly more potent than hirudin alone. The fibrin-deposition curves for hirudin at 44 ATU/ml and the mixture at 43 ATU/ml were indistinguishable. Hirudin at 10 ATU/ml and the mixture at 9 ATU/ml were also indistinguishable. All curves depicting inhibitor activity were significantly different from the NaCl control curve ($p < 0.00005$). Fibrin deposition for hirudin at 44 ATU/ml was lower than that for the mixture at 9 ATU/ml ($p = 0,003$). Deposition for the mixture at 43 ATU/ml was lower than that for hirudin at 10 ATU/mll ($p = 0.01$).

The hirudin-58D8-Fab' conjugate was shown to have a molecular mass of 57 kDa, corresponding to a 1:1 molar ratio of hirudin and 59D8-Fab'. Densitometric quantitation revealed that for each mole of conjugate, one mole of uncoupled 59D8-Fab' was present in the final preparation. Compared to uncoupled hirudin in a quantitative assay measuring (as reflected by thrombin inhibition) an anti-thrombin's ability to bind to β-peptide (as a surrogate for the amino-terminus of the fibrin beta-chain) or to immobilized fibrin, the hirudin-59D8-Fab' conjugate delivered more anti-thrombin activity than did hirudin in the presence of the target molecule, fibrin. Hirudin-59D8-Fab' conjugate proved to be more potent than hirudin or a mixture of hirudin and 59D8-Fab' in the prevention of thrombus growth either in a fibrinogen solution or in human plasma.

The increased local concentration of hirudin and the superior inhibition of thrombus growth by the hirudin 59DS-Fab' conjugate is attributed to antibody targeting of the chimeric molecule. Enhanced thrombin inhibition could only be demonstrated with the conjugate; an uncoupled mixture of hirudin and 59D8-Fab' was indistinguishable from hirudin. Thus, the enhancement of anti-thrombin activity demonstrated for the conjugate cannot be attributed to residual free 59DS-Fab' in the final conjugate preparation.

Importantly, there was no apparent difference between hirudin-59D8-Fab' conjugate and hirudin-59D8-IgG conjugate. Both were equally superior to uncoupled hirudin, indicating that one antibody binding site is enough to achieve the full targeting effect. This is particularly important with respect to the therapeutic use of a genetically engineered hybrid molecule consisting of 59D8-Fab' and hirudin.

Example 2: Recombinant hybrid antithrombotic reagents Recombinant Hirudin-59D8 antibody The construction of the recombinant hirudin-antibody hybrid expression vector was accomplished using the vector pSV2gpt, containing the pUC 12 polylinker inserted into the EcoR1-PstI site. An XbaI fragment containing the mouse γ-2b heavy chain constant region was inserted into the polylinker. Constructs containing antibody 59D8 sequence have the cloned heavy chain rearrangement of 59D8 inserted into a unique EcoR1 site 5' to the constant region sequence. In the original construct, portions of the γ-2b constant were removed and replaced with a sequence encoding plasminogen activator as described in Runge et al., Proc. Natl. Acad. Sci. USA 88:10337–10341, 1991, herein incorporated by reference. To make a hirudin-antibody hybrid, the plasminogen activator sequence was replaced with a cDNA sequence encoding hirudin (Harvey et al., Proc. Natl. Acad. Sci. USA 83:1084–1088, 1986), using recombinant cloning methods well known in the art.

Some constructs include the factor Xa recognition sequence (5'ATA GAA GGA CGA AGC 3') (SEQ ID NO:12) between the 59D8 heavy chain and the hirudin cDNA to allow proteolytic cleavage by Factor Xa of the recombinant protein into its two functional units to study their respective activities. The vectors were transfected into 59D8 heavy chain loss variant hybridoma cells by electroporation for expression of the recombinant hirudin-antibody hybrid and selected for expression of the recombinant hybrid protein.

Hybrid molecules can be purified from the culture media by two steps of affinity chromatography. Culture supernatant can be chromatographed on a β-peptide-Sepharose column. The eluate from the β-peptide-Sepharose column, containing recombinant hybrid molecules in which the 59D8 portion is functional, can then be chromatographed using a thrombin-Sepharose column. This purification scheme ensures that both moieties of the hybrid molecule possess their correct function.

Example 3: Pharmaceutical use of chemically conjugated or recombinant targeted anti-thrombin protein reagents For the treatment of patients in thrombogenic situations, including but not limited to coronary stent implantation and PTCA, chimeric proteins of the invention, generated by chemical conjugation or expression of recombinant hybrid proteins, can be administered in a pharmaceutically acceptable carrier such as physiological saline, in a manner similar to those presently used for the administration of streptokinase or tpa. The chimetic proteins can be administered intraperitoneally, intramuscularly, subcutaneously, or intravenously. It is expected that the preferred route of administration is intravenous, with a dosage of approximately 0.001–0.5 mg/kg of body weight per day; the chimera of the invention can be advantageously administered locally within the blood vessel at the site of expected clot formation.

The invention also includes an ex vivo method of therapy. This method of the invention would be of particular benefit in situations in which the blood of a patient is removed for filtering (e.g., kidney dialysis) or gas exchange procedures, or when the patient requires blood transfusions. For treatment of blood extracorporeally, blood can be removed from the individual using methods known to those skilled in the art, such as venous puncture. The chimeric protein in a physiologically acceptable carrier can then be mixed with the blood, and subsequently returned to the individual using methods known to those skilled in the art, such as intravenous drip.

In some cases, it can be useful to dissolve existing thrombotic occlusions in addition to preventing the formation of new clots. Administration of the chimeric protein of the invention with either (1) a fibrinolytic agent such as streptokinase, staphylokinase, urokinase, or tpa, or (2) a second chimeric protein containing a fibrin-binding domain linked to a fibrinolytic agent, would then be appropriate. The production of a chimeric protein containing a fibrin-binding domain linked to a fibrinolytic agent has been described (Haber et al., U.S. Pat. No. 5,116,613, herein incorporated by reference). These agents can be administered to a patient sequentially or simultaneously as described above.

Example 4: Pharmaceutical use of recombinant hybrid DNA reagents

Patients in thrombogenic situations may be treated by administering the nucleic acid of the invention, such that the expression and secretion of the chimeric protein takes place in the cells of the patient, such as blood cells. The nucleic acid of the invention may be introduced into target cells of a patient by standard vectors and/or gene delivery systems. Suitable gene delivery systems include liposomes, receptor-mediated delivery systems, naked DNA, and viral vectors such as herpes viruses, retroviruses, and adenoviruses, among others.

The invention also includes cells transfected with the DNA of the invention. Standard methods for transfecting cells with isolated nucleic acid are well known to those skilled in the art of molecular biology. Preferably, the cells are blood cells, such as antibody-producing B cells, and they express a chimeric protein of the invention encoded by the nucleic acid of the invention.

A therapeutic composition is provided which includes a pharmaceutically acceptable carrier and a therapeutically effective amount of a nucleic acid, wherein the nucleic acid includes a promoter operatively linked to a sequence encoding the recombinant chimeric protein of the invention, to generate high-level expression of the chimeric protein in cells transfected with the nucleic acid. The therapeutic composition may also include a gene delivery system as described above. Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the hybrid nucleic acid molecules of the invention will vary, but a preferred dosage for intravenous administration is approximately from $10^6$ to $10^{22}$ copies of the nucleic acid molecule.

Other embodiments:

For prevention of thrombotic occlusion post-operatively, a bio-polymer delivery system designed for the slow release of the chimeric protein of the invention may be implanted in close proximity to blood vessels that have been injured, such as those involved in coronary bypass surgery or coronary stent implantation. Such bio-polymer delivery systems are well known in the art (see, e.g., Folkman et al., U.S. Patent 4,164,560, herein incorporated by reference). The stent itself can be made of a bio-polymer that has been impregnated with the chimeric protein of the invention, and which therefore mediates slow local release of the protein to prevent restenosis of the blood vessel.

Other embodiments are within the following claims.

---

What is claimed is:

1. A chimeric molecule comprising a fibrin specific antibody or a fibrin-binding portion of a fibrin specific antibody linked by a covalent bond to an inhibitor of thrombin.

2. The molecule of claim 1, wherein said antibody is a monoclonal antibody specific for the amino terminus of the fibrin $\beta$ chain.

3. The molecule of claim 1, wherein said antibody is monoclonal antibody 59D8 (ATCC Accession No HB 8546).

4. The molecule of claim 1, wherein said inhibitor of thrombin is hirudin.

5. The molecule of claim 1, wherein said inhibitor of thrombin is a thrombin-inhibiting fragment of hirudin.

6. The molecule of claim 5, wherein said fragment has been chemically modified to contain a sulfate, carboxylate, sulfonate, phosphonate, carbonate, methyl sulfonate or methyl phosphonate group.

7. The molecule of claim 1, wherein said inhibitor of thrombin is selected from the group consisting of antithrombin III; $\beta$, $\beta'$ monochlormethylene diadenosine $5'5'''$-$p^1p^4$-tetraphosphate; Ac-(D)Phe-Pro-boroArg-OH; Boc-(D)Phe-Pro-boroArg-$C_{10}H_{16}$; H-(D)Phe-Pro-boroArg-OH; H-(D)Phe-Pro-boroArg-$C_{10}H_{16}$; D-Phe-Pro-Arg; [Asn-Gly-Asp-Phe-Glu-Glu-Ile-Pro-Glu-Glu-Tyr(OS)$_3$)-Leu; [D -Phe-Pro-Arg-Pro-(Gly)$_4$-Asn-Gly-Asp-Phe-Glu-Glu-Ile-Pro-Glu -Glu-Tyr-Leu]; 2,3,-dialkylindoles 3,4, -dihydro-3-benzyl-6-chloromethylcoumarin; D-phenylalanyl-prolyl-arginine chloromethyl ketone-treated $\alpha$-thrombin; D-Phe-Pro-Arg-H; D -Phe-Pro-Arg-CH$_2$Cl; N$\alpha$- ($\beta$-naphthylsulfonylglycyl) -4-amidinophenylalanine piperidide; (2R, 4R)-4-methyl-1-[N$^\alpha$-(3-methyl-1,2,3,4-tetrahydro-8-quinolinesulphonyl) -L-arginyl]-2-piperidine carboxylic acid; N$^\alpha$-acetyl[D-Phe$^{45}$, Arg$\Psi$(COCH$_2$)$^{47}$, Gly$^{48}$-]desulfo hirudin$^{45-65}$; Hirutonin-1; Hirutonin-2; Hirutonin-3; and Hirutonin-4.

8. The molecule of claim 1, wherein said binding portion is a fibrin-specific Fab' fragment.

9. The molecule of claim 1, wherein said binding portion is a fibrin-specific Fv fragment.

10. The molecule of claim 1, wherein said molecule comprises a fibrin-specific antibody linked by a covalent bond to an inhibitor of thrombin.

11. A pharmaceutical composition useful for inhibiting thrombin activity, comprising the molecule of claim 1 in a pharmaceutically acceptable carrier.

12. A composition comprising (a) the molecule of claim 1, (b) a chimeric molecule comprising a fibrin-binding portion of a second antibody linked by a second covalent bond to a thrombolytic agent and (c) an acceptable carrier.

13. The composition of claim 12, wherein said first antibody is identical to said second antibody.

14. The composition of claim 12, wherein said thrombolytic agent is selected from the group consisting of streptokinase, staphylokinase, urokinase, or tissue-type plasminogen activator.

* * * * *

UNITED STATES PATENT AND TRADEMARK OFFICE
CERTIFICATE OF CORRECTION

PATENT NO.  : 5,443,827

DATED       : August 22, 1995

INVENTOR(S) : Edgar Haber, Christoph Bode, Marschall S. Runge

It is certified that error appears in the above-identified patent and that said Letters Patent is hereby corrected as shown below:

Column 5, line 8, replace "10 ATU/ml (  -  )" with --10 ATU/ml (◇-◇)--

Column 5, line 21, replace "9 ATU/ml-  ;" with --9 ATU/ml (■-■);--

Column 6, line 45, replace "e-thrombin" with --α-thrombin--;

Column 6, line 50, replace "Ne-(ß-naphthyl-sulfonylglycyl)" with --Nα-(ß-naphthylsulfonylglycyl)--;

Column 8, line 19, replace "Chimetic" with --Chimeric--;

Column 8, line 39, replace "59DS-IgG conjugate" with --59D8-IgG conjugate--;

Column 8, line 40, replace "59DSFab' conjugate" with --59D8-Fab' conjugate--;

Column 8, line 43, replace "59DS-IgG" with --59D8-IgG--;

UNITED STATES PATENT AND TRADEMARK OFFICE
CERTIFICATE OF CORRECTION

PATENT NO. : 5,443,827

DATED : August 22, 1995

INVENTOR(S) : Edgar Haber, Christoph Bode, Marschall S. Runge

It is certified that error appears in the above-identified patent and that said Letters Patent is hereby corrected as shown below:

Column 8, line 44, replace "59DS-Fab'" with --59D8-Fab'--;

Column 8, line 61, replace at both occurrences "59DS-IgG" with --59D8-IgG--;

Column 11, line 44, replace "59DS-IgG" with --59D8-IgG--;

Column 11, line 66, replace "59DS-IgG" with --59D8-IgG--;

Column 11, line 67, replace "59DS-IgG or 59DS-Fab'" with --59D8-IgG or 59D8-Fab'--;

Column 12, line 8, replace "59DS-Fab'" with --59D8-Fab'--;

Column 12, line 14, replace "59DS-Fab'" with --59D8-Fab'--;

Column 12, line 29, replace "59DS-Fab'" with --59D8-Fab'--;

Column 13, line 21, replace "thromhus" with --thrombus--;

UNITED STATES PATENT AND TRADEMARK OFFICE
CERTIFICATE OF CORRECTION

PATENT NO. : 5,443,827

DATED : August 22, 1995

INVENTOR(S) : Edgar Haber, Christoph Bode, Marschall S. Runge

It is certified that error appears in the above-identified patent and that said Letters Patent is hereby corrected as shown below:

Column 13, line 55, replace "59DS-Fab'" with --59D8-Fab'--;

Column 14, line 25, replace "9 ATU/ml (p=0,003)" with --9 ATU/ml (p=0.003)--;

Columns 17-18, SEQUENCE LISTING, correct Seq. ID Nos. 1, 2, and 3 as follows:

| Val 1 | Val | Tyr | Thr | Asp 5 | Cys | Thr | Glu | Ser | Gly 10 | Gln | Asn | Leu | Cys | Leu 15 | Cys |
|---|---|---|---|---|---|---|---|---|---|---|---|---|---|---|---|
| Glu | Gly | Ser | Asn 20 | Val | Cys | Gly | Gln | Gly 25 | Asn | Lys | Cys | Ile | Leu 30 | Gly | Ser |
| Asp | Gly | Glu | Lys 35 | Asn | Gln | Cys | Val 40 | Thr | Gly | Glu | Gly | Thr 45 | Pro | Lys | Pro |
| Gln | Ser 50 | His | Asn | Asp | Gly | Asp 55 | Phe | Glu | Glu | Ile | Pro 60 | Glu | Glu | Tyr | Leu |
| Gln 65 | | | | | | | | | | | | | | | |

UNITED STATES PATENT AND TRADEMARK OFFICE
CERTIFICATE OF CORRECTION

PATENT NO. : 5,443,827

DATED : August 22, 1995

INVENTOR(S) : Edgar Haber, Christoph Bode, Marschall S. Runge

It is certified that error appears in the above-identified patent and that said Letters Patent is hereby corrected as shown below:

Columns 17-18, SEQUENCE LISTING, correct Seq. ID Nos. 1, (2) and 3 as follows:

| Ile 1 | Thr | Tyr | Thr | Asp 5 | Cys | Thr | Glu | Ser | Gly 10 | Gln | Asn | Leu | Cys | Leu 15 | Cys |
| Glu | Gly | Ser | Asn 20 | Val | Cys | Gly | Lys | Gly 25 | Asn | Lys | Cys | Ile | Leu 30 | Gly | Ser |
| Gln | Gly | Lys 35 | Asp | Asn | Gln | Cys | Val 40 | Thr | Gly | Glu | Gly | Thr 45 | Pro | Lys | Pro |
| Gln | Ser 50 | His | Asn | Gln | Gly | Asp 55 | Phe | Glu | Pro | Ile | Pro 60 | Glu | Asp | Ala | Tyr |
| Asp | Glu 65 | | | | | | | | | | | | | | |

UNITED STATES PATENT AND TRADEMARK OFFICE
CERTIFICATE OF CORRECTION

PATENT NO. : 5,443,827

DATED : August 22, 1995

INVENTOR(S) : Edgar Haber, Christoph Bode, Marschall S. Runge

It is certified that error appears in the above-identified patent and that said Letters Patent is hereby corrected as shown below:

Columns 17-18, SEQUENCE LISTING, correct Seq. ID Nos. 1, 2, and 3 as follows:

```
Asp Cys Thr Glu Ser Gly Gln Asn Leu Cys Leu Cys Glu Gly Ser Asn
 1               5                    10                   15

Val Cys Gly Gln Gly Asn Lys Cys Ile Leu Gly Ser Asp Gly Glu Lys
            20              25                  30

Asn Gln Cys Val Thr Gly Glu Gly Thr Pro Lys Pro Gln Ser His Asn
        35              40                  45

Asp Gly Asp Phe Glu Glu Ile Pro Glu Glu
    50              55
```

Signed and Sealed this

Twenty-eighth Day of November 1995

Attest:

Attesting Officer

BRUCE LEHMAN

Commissioner of Patents and Trademarks